(12) United States Patent
Zhu et al.

(10) Patent No.: US 12,221,399 B2
(45) Date of Patent: Feb. 11, 2025

(54) EXIGUOBACTERIUM INDICUM AND APPLICATION THEREOF IN SYNTHESIS OF NANO-SELENIUM

(71) Applicant: JIANGSU ACADEMY OF AGRICULTURAL SCIENCES, Jiangsu (CN)

(72) Inventors: Yanyun Zhu, Jiangsu (CN); Hongmei Jin, Jiangsu (CN); Gary Banuelos, Fresno, CA (US); Yiwei Dong, Jiangsu (CN); Ning Zhu, Jiangsu (CN); Xiangyang Yu, Jiangsu (CN)

(73) Assignee: JIANGSU ACADEMY OF AGRICULTURAL SCIENCES, Jiangsu (CN)

( * ) Notice: Subject to any disclaimer, the term of this patent is extended or adjusted under 35 U.S.C. 154(b) by 0 days.

(21) Appl. No.: 18/559,060

(22) PCT Filed: Jul. 20, 2022

(86) PCT No.: PCT/CN2022/106875
§ 371 (c)(1),
(2) Date: Nov. 6, 2023

(87) PCT Pub. No.: WO2023/020191
PCT Pub. Date: Feb. 23, 2023

(65) Prior Publication Data
US 2024/0228391 A1    Jul. 11, 2024

(30) Foreign Application Priority Data

Aug. 17, 2021 (CN) .......................... 202110941393.6

(51) Int. Cl.
| | | |
|---|---|---|
| *C05D 9/00* | (2006.01) |
| *A61K 33/04* | (2006.01) |
| *B82Y 40/00* | (2011.01) |
| *C12N 1/20* | (2006.01) |
| *C12P 3/00* | (2006.01) |
| *C12R 1/01* | (2006.01) |

(52) U.S. Cl.
CPC ................ *C05D 9/00* (2013.01); *A61K 33/04* (2013.01); *B82Y 40/00* (2013.01); *C12N 1/20* (2013.01); *C12N 1/205* (2021.05); *C12P 3/00* (2013.01); *C12R 2001/01* (2021.05)

(58) Field of Classification Search
CPC ................................... C12P 3/00; C05F 11/08
See application file for complete search history.

(56) References Cited

U.S. PATENT DOCUMENTS

2009/0298165 A1    12/2009   Wiedemann et al.

FOREIGN PATENT DOCUMENTS

| CN | 106479927 | | 3/2017 |
|---|---|---|---|
| CN | 112725230 | | 4/2021 |
| CN | 113173828 A | * | 7/2021 |
| CN | 113637608 | | 11/2021 |
| WO | 2015077278 | | 5/2015 |

OTHER PUBLICATIONS

Javed et al. Chemical Speciation & Bioavailability, 2016, vol. 27, No. 4, 162-168 (Year: 2016).*
Yin, Xian et al., "Research progress in microbial enrichment of organic selenium", Food and Fermentation Industries, Dec. 1, 2020, with English abstract, pp. 259-266, vol. 47, No. 5.
"International Search Report (Form PCT/ISA/210) of PCT/CN2022/106875", mailed on Oct. 14, 2022, with English translation thereof, pp. 1-6.

* cited by examiner

*Primary Examiner* — Louise W Humphrey
*Assistant Examiner* — Jessica Faye Edwards
(74) *Attorney, Agent, or Firm* — JCIPRNET

(57) ABSTRACT

An *Exiguobacterium indicum* YAN2 having high-concentration selenite tolerance, the preservation number thereof being GDMCC No. 61594, and a method for fermenting inorganic selenium into nano-selenium by using the strain are provided. The obtained nano-selenium can promote the growth of leaf vegetables, increase the content of chlorophyll, Vc, and total phenol, etc, reduce the content of nitrate, and improve the quality of leaf vegetables. In addition, the present application further provides a nano-selenium liquid fertilizer prepared by fermentation using the strain.

4 Claims, 4 Drawing Sheets

Specification includes a Sequence Listing.

EXIGUOBACTERIUM INDICUM AND APPLICATION THEREOF IN SYNTHESIS OF NANO-SELENIUM

CROSS-REFERENCE TO RELATED APPLICATION

This is a 371 application of the International PCT application serial no. PCT/CN2022/106875, filed on Jul. 20, 2022, which claims the priority benefits of China Application No. 202110941393.6, filed on Aug. 17, 2021. The entirety of each of the above-mentioned patent applications is hereby incorporated by reference herein and made a part of this specification.

BACKGROUND

Technical Field

The present disclosure belongs to the technical fields of microbial technology and biological nano-selenium preparation, and particularly relates to a strain of *Exiguobacterium indicum* and application thereof in the biosynthesis of nano-selenium and the improvement of crop quality.

Description of Related Art

Selenium (Se) is one of the essential trace elements for the growth and metabolism of human and animals, and is the functional core of a variety of selenium-containing enzymes.

Selenium deficiency in human body is prone to cause many diseases. Existing studies have made it clear that cardiovascular and cerebrovascular diseases, diabetes, Keshan disease, Kaschin-Beck disease and reproductive system diseases are related to selenium deficiency. From a global perspective, there are selenium-deficient zones respectively located above 30° N and above 30° S, involving over 40 countries. In China, about 73% of the territory is in the areas with low (deficient) selenium, and the probability of local people suffering from diseases is much higher than that of other areas. Therefore, it is of great significance to find effective means and methods for selenium supplement. At present, people mainly take selenium supplements in an inorganic form through external sources. However, the effective range of selenium is extremely narrow, and excessive selenium may easily lead to selenium poisoning in human or animal bodies, and even cause death.

Nano-selenium is a kind of red elemental selenium [Se (0)] with nanometer size. Compared with ordinary elemental selenium, it is more easily absorbed and utilized by the human body, and its toxicity is generally lower than that of inorganic selenium and organic selenium. Due to its difference from the inorganic selenium, the organic selenium, and the ordinary elemental selenium, it was earlier named nano-selenium (Nano-Se) by German scientists. Compared with selenate [Se(VI)], selenite [Se(IV)], seleno-amino acid [Se(-II)], and the like, nano-selenium has higher biological activity and safety. At present, the mainstream nano-selenium synthesis methods include chemical synthesis and biosynthesis. Generally, nano-selenium synthesized by biological methods is more stable than that synthesized by chemical methods, has stronger tolerance to environmental temperature, acidity, alkalinity, and the like, and is not easy to age into black elemental selenium after being stored for a long time.

In nature, microorganisms play an important role in the related transformation processes of different forms of selenium. Some of the microorganisms can also transform highly toxic selenite or selenate into red elemental nano-selenium. Compared with the process of chemical synthesis of nano-selenium, microbial synthesis of nano-selenium is low in energy consumption, causes less pollution, and is simple and economical.

The bacteria that have been reported to have a nano-selenium synthesis ability include *Enterobacter* sp., *Rhodobacter* sp., *Brevibacterium* sp., *Streptomyces* sp., *Rahnella* sp., etc. However, the habitats of these strains are relatively narrow, resulting in corresponding limitations in their nanosynthesis and application development. *Exiguobacterium* sp. belongs to probiotics and is a facultative anaerobe that can grow in a temperature range of −12° C. to 55° C., thus having a broad habitat. Researchers at home and abroad have separated out different *Exiguobacterium* sp. from a variety of environments, which have been applied in the fields such as environmental remediation, plant growth promotion, and pathogen prevention and control. At present, there is no report on the application of *Exiguobacterium* sp. in synthesis of nano-selenium.

SUMMARY

In view of the above-mentioned problems, the examples of this application provide a strain of *Exiguobacterium indicum*, and a method for synthesizing nano-selenium by fermenting the strain.

This application is completed by using the following technical solution.

First of all, this application provides a strain of *Exiguobacterium indicum* with a preservation number of GDMCC NO. 61594. This strain is now preserved in the Guangdong Microbial Culture Collection Center (GDMCC), with the preservation date of Apr. 2, 2021. The preservation address of the strain is Guangdong Institute of Microbiology, 5$^{th}$ Floor, Experiment Building, Yard No. 100, Xianlie Middle Road, Yuexiu District, Guangzhou City, Guangdong Province, China, Postcode: 510070.

The *E. indicum* YAN2 was separated out by the inventor from the soil of Fengsan Town Mining Area, Kaiyang County, Guiyang City, Guizhou Province on Oct. 1, 2020. Its colony is round with regular edges and smooth surfaces, moist, yellow, raised, and easy to pick up. The 16SrDNA sequence of the strain was determined, and in combination with the results of phylogenetic analysis and physiological and biochemical identification, the strain was determined to be *E. indicum*, which was named YAN2 by the applicant. The *E. indicum* can produce spherical biosynthetic nano-selenium (Bio-SeNP) in a selenium-containing medium.

Secondly, one example of this application provides a method for the biosynthesis of nano-selenium by using the *E. indicum* with the preservation number of GDMCC NO. 61594. The method specifically includes the following steps:

1) inoculating the *E. indicum* with the preservation number of GDMCC NO. 61594 into an LB liquid medium, and performing activated culture until $OD_{600}$ is approximately equal to 1.0 to obtain activated bacteria liquid for later use;

2) inoculating the activated bacteria liquid obtained in step 1) into a fermentation tank containing an inorganic selenium fermentation medium at an amount of inoculation by a volume ratio of 2.5±0.2% (v/v), where a fermentation temperature is 30±1° C., a stirring speed is 150±5 rpm, a volume of fermentation broth: a volume of aeration per minute=1:0.5, and a tank pressure is 1.0±0.4 F/cm$^2$, and carrying out fermentation (for about 60-120 h) until the bacterial protein content is 0.4-0.6 mg/mL to obtain fermented bacteria liquid, where the fermentation medium is obtained by taking 5 g of a yeast extract, 10 g of tryptone, and 10 g of NaCl, and adding deionized water to make up to 1 L; autoclaving at 121° C. for 20 min; and then adding a 1 M sterile selenite solution to make the final concentration of selenite in the medium to be 5 mM; and 3) centrifuging the fermented bacteria liquid at 8000-10000 rpm for 10-15 min, and collecting precipitate to obtain nano-selenium.

The fermentation medium is obtained by taking 5 g of a yeast extract, 10 g of tryptone, 10 g of NaCl, and 5 mM sodium selenite, and adding deionized water to make up to 1 L; and autoclaving at 121° C. for 20 min.

In practical applications, the obtained nano-selenium can also be further prepared by any conventional method in the art to obtain nano-selenium powder. For example, the precipitate obtained in step 3) is washed with sterile normal saline for 3-4 times (ultrasonic treatment is performed for 10 min after each washing), the precipitate is resuspended with sterile water in an amount being 1/20 of the volume of fermentation broth, and the obtained bacterial suspension is freeze-dried (at −10° C. to −50° C.), so that dry nano-selenium powder is obtained.

The nano-selenium obtained in step 3) can be used in the production of liquid/solid biological selenium fertilizers, health products, selenium-rich functional foods, and pharmaceutical products.

Thirdly, one example of this application further provides a nano-selenium liquid fertilizer, which is prepared by the following method:

1) inoculating the *E. indicum* with the preservation number of GDMCC NO. 61594 into an LB liquid medium, and performing activated culture until $OD_{600}$ is approximately equal to 1.0 to obtain activated bacteria liquid;

2) inoculating the activated bacteria liquid into a fermentation tank containing a selenium-containing TB fermentation medium (5 mM sodium selenite) at an amount of inoculation of 2.5±0.2% (v/v), where a fermentation temperature is 30±1° C., a stirring speed is 150±5 rpm, a volume of fermentation broth: a volume of aeration per minute=3:1, and a tank pressure is 1.2±0.2 F/cm², and carrying out fermentation (for about 5-6 d) until an amount of nano-selenium synthesis reaches a stable level to obtain a fermented liquid fertilizer, where the selenium-containing TB fermentation medium is prepared by taking 24 g of a yeast extract, 20 g of tryptone, 4 ml of glycerol, 72 mM $K_2HPO_4$, and 17 mM $KH_2PO_4$, and adding deionized water to make up to 1 L; autoclaving at 121° C. for 20 min, cooling to room temperature, and adding 5 mL of 1 M sterile selenite ($Na_2SeO_3$) mother liquor; and 3) centrifuging the fermented liquid fertilizer at 10000 rpm for 15 min, and collecting precipitate, cleaning (washing with sterile normal saline for 3-4 times), and then resuspending the precipitate with sterile water in an amount being 1/20 of a volume of the fermented liquid fertilizer to obtain the nano-selenium liquid fertilizer.

The examples of this application have proved that the nano-selenium liquid fertilizer can significantly increase the selenium content of leafy vegetables and other crops. When the nano-selenium is applied to green vegetables and the treatment concentration of nano-selenium is 1-10 mg/L, the selenium contents of the green vegetables are 3.2-62.31 times higher than that of the blank group; the Vc contents of the green vegetables are increased by 13.93-45.91% compared with the blank group; the total phenol contents of the green vegetables are increased by 12.87-28.59% compared with the blank group; the fresh weights of the green vegetables are increased by 6.11-29.35% compared with the blank group; and the contents of antioxidant activity indicators POD, SOD and GSH-Px are respectively increased by 28.45-32.24%, 38.95-48.07% and 57.53-61.38% compared with the blank group.

In this application, the strain of *E. indicum* YAN2 was separated out for the first time, and the nano-selenium was synthesized by fermenting the strain due to its ability to tolerate selenite and characteristic of synthesizing nano-selenium. According to one example of this application, applying the nano-selenium can improve the quality and stress resistance of green vegetables, expand the planting range of selenium-rich vegetables, and enlarge the planting area of selenium-rich crops. Furthermore, the nano-selenium liquid fertilizer prepared in the examples of this application has the advantages of being green, safe, high in efficiency, and the like, and is high in activity, good in safety and convenient to apply when being applied to crops.

DESCRIPTION OF THE EMBODIMENTS

Figure 1:
FIG. 1 is a photo showing the colony morphology of *E. indicum* YAN2 on an LB medium.

The technical solutions of the present disclosure will be further described in detail below in conjunction with specific examples. The examples are only used to illustrate the technical solutions of the present disclosure, but not to limit them. Although the present disclosure has been described in detail with reference to the foregoing examples, it is still possible for those of ordinary skill in the art to modify the foregoing examples or replace some of them. These modifications or replacements will not cause the corresponding technical solutions to depart from the scope of the technical solutions claimed in the present disclosure.

Sequences Involved in the Examples:

```
SEQ ID NO. 1:
5'-AGAGTTTGATCMTGGCTCAG-3;
and

SEQ ID NO. 2:
5'-GGTTACCTTGTTACGACTT-3'.
```

Mediums Involved in the Examples:

Sterile selenite ($Na_2SeO_3$) mother liquor: 8.6 g of $Na_2SeO_3$ solid powder and 50 ml of deionized water were allowed to pass through a 0.2 μm filter membrane and then enter a sterile PE tube to obtain 1 M selenite mother liquor, and the obtained mother liquor was sealed at 4° C. for later use.

NA solid medium: 3 g of beef extract, 5 g of tryptone, 2.5 g of glucose, and 18 g agar were taken, and deionized water was added to make up to 1 L; and autoclaved sterilization was performed at 121° C. for 20 min.

Selenium-containing NA solid medium: 3 g of beef extract, 5 g of tryptone, 2.5 g of glucose, and 18 g agar were taken, and deionized water was added to make up to 1 L; autoclaved sterilization was performed at 121° C. for 20 min; and the product was dried by airing on an ultra-clean workbench until being cooled to about 55-65° C., and 5 mL of 1 M sterile selenite ($Na_2SeO_3$) mother liquor was added to obtain the solid medium.

LB solid medium: 5 g of a yeast extract, 10 g of tryptone, 10 g of NaCl, and 13 g agar were taken, and deionized water was added to make up to 1 L; and autoclaved sterilization was performed at 121° C. for 20 min.

LB liquid medium (fermented seed medium): 5 g of a yeast extract, 10 g of tryptone, and 10 g of NaCl were taken, and deionized water was added to make up to 1 L; and autoclaved sterilization was performed at 121° C. for 20 min.

Selenium-containing LB liquid medium (fermentation medium): Sterile selenite mother liquor was added into an LB liquid medium subjected to autoclaved sterilization to make the final concentration of selenate in the medium to be 5 mM, so that the liquid medium was obtained.

Selenium-containing TB fermentation medium: 24 g of a yeast extract, 20 g of tryptone, 4 ml of glycerol, 72 mM $K_2HPO_4$, and 17 mM $KH_2PO_4$ were taken, and deionized water was added to make up to 1 L; autoclaved sterilization was performed at 121° C. for 20 min; and the product was placed on an ultra-clean workbench until being cooled to room temperature, and 5 mL of 1 M sterile selenite ($Na_2SeO_3$) mother liquor was added to obtain the fermentation medium.

Reagents Involved in the Examples:

A yeast extract, tryptone, agar, and a beef extract are all purchased from Nanjing Dulai Biotechnology Co., Ltd.; and in this application, selenite specifically refers to sodium selenite ($Na_2SeO_3$), and sodium selenite, NaCl, glucose, glycerol, $K_2HPO_4$, $KH_2PO_4$, $Na_2S$, etc. are all purchased from Sinopharm Group Industrial Co., Ltd.

Instruments Involved in the Examples:

High-pressure steam sterilization pot (MLS-3781L-PC, Panasonic), micro-centrifuge (5424, Eppendorf), constant temperature culture shaker (HYG-A, Taicang, Jiangsu), biochemical incubator (LRH-250, Shanghai Yiheng), ultra-clean workbench (Beijing Yatai Kelong), constant temperature water bath pot (DK-8D, Shanghai Jinghong), vacuum dryer (EM-CPD030, Leica, Germany), scanning electron microscope (S-4800, Hitachi, Japan), and energy dispersive spectrometer (HT7700, Hitachi, Japan).

Unless otherwise specified, the reagents, materials, etc. involved in the following examples are all commercially available.

Example 1: Separation and Screening of Strain YAN2

10 g of mining soil (derived from Fengsan Town Mining Area, Kaiyang County, Guiyang City, Guizhou Province) was taken and put into a conical flask filled with 90 mL of sterile normal saline, and was then oscillated at 25° C. and 150 rpm for 30 min to obtain a $10^{-1}$ soil suspension. 10 mL of the $10^{-1}$ soil suspension was taken and added into a conical flask filled with 90 mL of sterile normal saline to obtain $10^{-2}$ soil diluent. By analogy, $10^{-3}$ soil diluent, $10^{-4}$ soil diluent and $10^{-5}$ soil diluent were prepared, respectively. Then, a pipette was used to respectively pipette 100 μL of the $10^{-3}$ soil diluent, 100 μL of the $10^{-4}$ soil diluent and 100 μL of the $10^{-5}$ soil diluent to selenium-containing beef extract peptone (NA) solid mediums, and each of the solid mediums was coated with the soil diluent evenly, with three repeats for each gradient. Finally, all the coated plates were placed upside down in a constant temperature incubator at 30° C. for 2-4 d. The changes on the mediums were observed every day. If there were single colonies, the medium was placed on an ultra-clean workbench, and the larger and red single colony was picked up by using a sterile inoculation loop, and then was transferred and inoculated into a selenium-free LB solid medium for purification. After purification for 3-5 generations, the single colony was transferred and inoculated into an LB liquid medium, and subjected to constant temperature incubation at 30° C. and 150 rpm until reaching a logarithmic phase ($OD_{600}$≈1.0) to obtain a fresh bacterial suspension. According to a ratio of bacterial suspension to glycerol being 3:7, the bacterial suspension was mixed with sterile glycerol, and the mixture was stored in an ultra-low temperature refrigerator at −80° C. for later use. The applicant named this strain as YAN2.

Example 2: Identification of Strain YAN2

Universal primers for bacteria 27F (whose nucleotide sequence was shown in SEQ ID NO. 1) and 1492R (whose nucleotide sequence was shown in SEQ ID NO. 2) were used to amplify the 16S rRNA gene of a strain YAN2.

A PCR reaction system includes: a template DNA, 1.5 μL; dd$H_2O$, 21.5 μL; 27F, 1.0 μL; 1492R, 1.0 μL; and Taq enzyme (Mix), 25 μL.

PCR reaction conditions were: pre-denaturation at 94° C. for 10 min; denaturation at 94° C. for 1 min, annealing at 58° C. for 1 min, and extension at 72° C. for 2 min, a total of 35 cycles; and extension at 72° C. for 10 min. Transient centrifugation and storage at 4° C. for later use.

The obtained PCR products were sent to Nanjing Qingke Biotechnology Co., Ltd. for sequencing.

The appearance of the colony morphology of the strain YAN2 on an LB solid medium is shown in FIG. 1. The physiological and biochemical properties of this strain are shown in Table 1. The results of catalase, V-P reaction, and nitrate reduction test are all positive, and the results of methyl red test and starch hydrolysis are all negative.

TABLE 1

Physiological and biochemical properties of strain YAN2

| Strain number | Catalase | V—P reaction | Methyl red test | Nitrate reduction | Gelatin hydrolysis |
|---|---|---|---|---|---|
| YAN2 | + | + | − | + | − |

Figure 2:
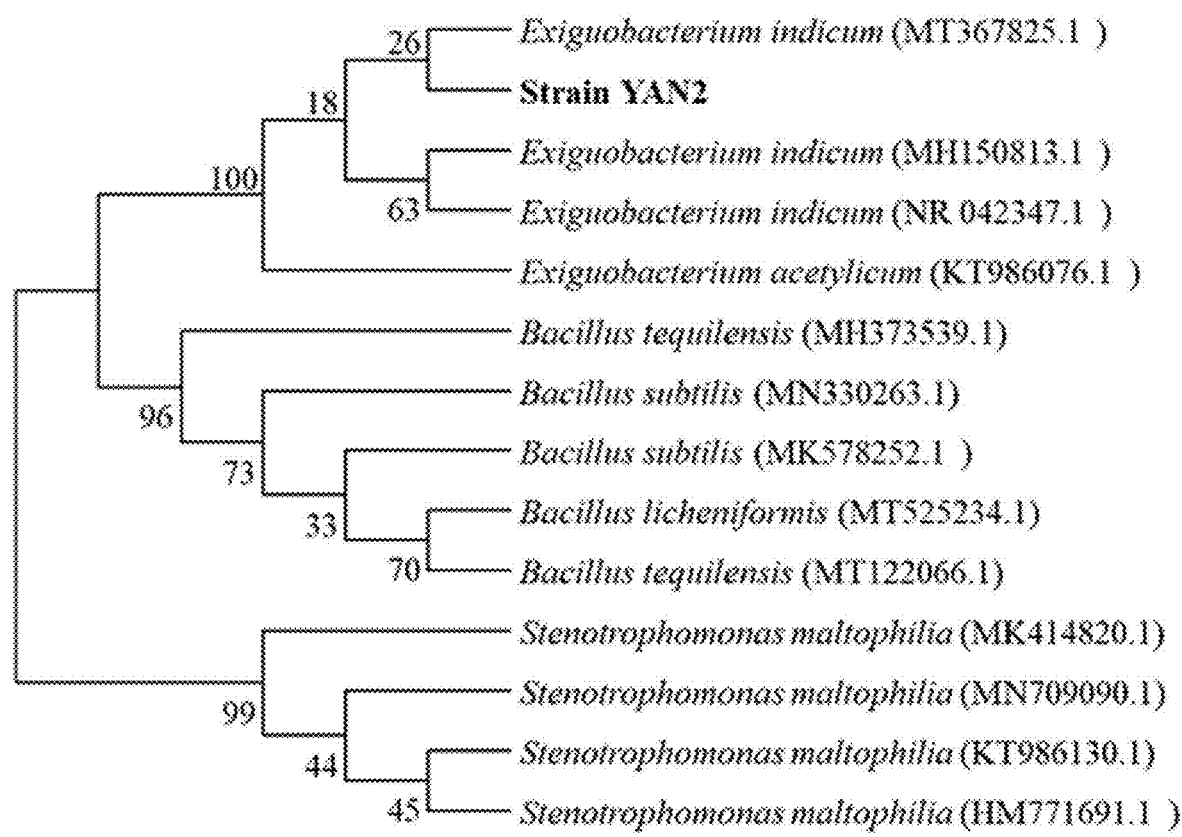
FIG. 2 is a schematic diagram of a phylogenetic tree of 16S rRNA gene of *E. indicum* YAN2.

Through the sequence analysis for the 16S rRNA of the strain YAN2, the BLAST comparison in NCBI shows that the strain has a higher homology with *E. indicum*, with a similarity being 95%. A phylogenetic tree of the 16S rRNA of the strain YAN2 is shown in FIG. 2, and combined with its appearance and physiological and biochemical properties, the strain YAN2 is preliminarily identified as the *E. indicum*.

The strain with a preservation number of GDMCC NO. 61594 is applied to be preserved in the Guangdong Microbial Culture Collection Center (GDMCC) on Apr. 2, 2021. The preservation address of the strain is Guangdong Institute of Microbiology, 5$^{th}$ Floor, Experiment Building, Yard No. 100, Xianlie Middle Road, Yuexiu District, Guangzhou City, Guangdong Province, China, Postcode: 510070.

Example 3: Analysis on Selenium Tolerance of *E. indicum* YAN2

Figure 3:
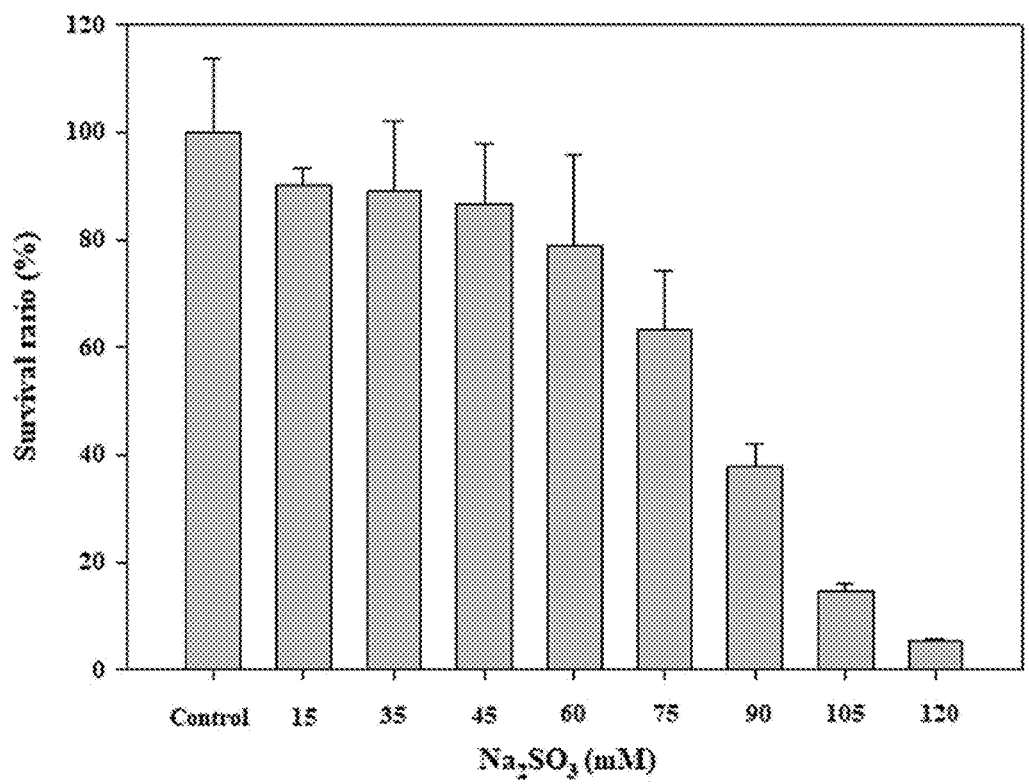
FIG. 3 shows the results of a selenium tolerance test for *E. indicum* YAN2.

*E. indicum* YAN2 was incubated into an LB medium, and cultured on a shaker at 30° C. and 150 rpm. When the value of $OD_{600}$ was 1, gradient dilution was carried out on bacteria liquid. First, 100 μL of the bacteria liquid was absorbed and added to 900 μL of sterile water to obtain $10^{-1}$ diluent, and then by analogy to obtain $10^{-1}$-$10^{-6}$ diluent of the YAN2. A pipette was used to respectively pipette 2.5 μL of the $10^{-3}$ diluent, 2.5 μL of the $10^{-4}$ diluent, 2.5 μL of the $10^{-5}$ diluent, and 2.5 μL of the $10^{-6}$ diluent to LB solid mediums with different selenium concentrations, with four replicates for each gradient. Stationary culture was performed at 28-35° C. and the growth was observed. After 96 h, the number of colonies was counted so as to calculate the survival rate (SR). The selenium tolerance performance of the strain is shown in FIG. 3.

The concentration of selenium having a survival rate within a range of 5%-15% is defined as the minimum sub-inhibitory concentration. From the results in FIG. 3, it can be seen that the minimum sub-inhibitory concentration of strain YAN2 is 105-120 mM, and the concentration of the strain YAN2 tolerant to selenite can reach 120 mM.

Example 4: The Dynamic Law of Biological Nano-Selenium Synthesis by *E. indicum* YAN2

Nano-selenium was prepared by the following steps:
1) initial strain activation: a single colony was picked up from an LB solid plate of YAN2 and inoculated into a fermentation seed medium, and constant temperature incubation was performed at 30±1° C. and 150±5 rpm until reaching a logarithmic phase ($OD_{600}$≈1.0);
2) strain reactivation: the above-mentioned strain at the logarithmic phase was transferred and inoculated into a new fermentation seed medium according to an amount of inoculation of 0.5% (v/v), and cultured until reaching a logarithmic growth phase under the same conditions for later use; and
3) fermentation: according to an amount of inoculation of 2.5±0.2% (v/v), the bacteria liquid of the YAN2 at the logarithmic phase was transferred and inoculated into a selenium-containing TB fermentation medium, continuous shaking culture was carried out at 30±1° C. and 150±5 rpm, fermentation broth was taken every 6 h, and the contents of nano-selenium and YAN2 cell protein in the fermentation broth were measured until the end of the culture. The specific methods for the determination of nano-selenium content and cell protein content are described below.

The content of nano selenium was determined by a Biswas method (Biswas K C, Barton L L, Tsui W L, Shuman K, Gillespie J, Eze C S (2011) A novel method for the measurement of elemental selenium produced by bacterial reduction of selenite. J Microbiol Meth 86:140-144). The analysis steps were as follows: fermentation broth was centrifuged at 4° C. and 8000-12000 rpm for 10-15 min, the supernatant was removed, and the product was washed with a 1 M NaCl solution for 3 times, so that precipitate was obtained; then, a 1 M $Na_2S$ solution was added, and a volume ratio of the $Na_2S$ solution to the fermentation broth was 1:2; the mixture was enabled to react at room temperature for 1 h after being evenly mixed, and was centrifuged at 4° C. and 8000-12000 rpm for 5-10 min; and the supernatant was taken, and its absorbance value at 500 nm was measured, with three repetitions for each sample. According to a standard curve of nano-selenium absorbance, the contents of the nano-selenium in the fermentation broth at different time points were calculated.

The content of cell protein was determined by a modified Lowry method (Lowry O H, Rosebrough N J, Farr A L, Randall R J (1951) Protein measurement with the folin phenol reagent. J Biol Chem 193:265-275). The analysis steps were as follows: fermentation broth was centrifuged at 4° C. and 8000-12000 rpm for 10-15 min, the supernatant was removed, a 0.1 M NaOH solution was added and fully mixed, and a volume ratio of the NaOH solution to the fermentation broth was 5:8; the sample was placed in a boiling water bath to be treated for 10-15 min, and centrifuged at 8000-12000 rpm for 2-4 min; and the supernatant was taken, Coomassie Brilliant Blue was added to the supernatant in an amount being 50 times the volume of the supernatant for staining for 3-5 min, and the absorbance of the sample was measured at 595 nm, with three repetitions for each sample. According to a standard curve of cell protein absorbance, the contents of the cell protein in the fermentation broth at different time points were calculated.

Figure 4:
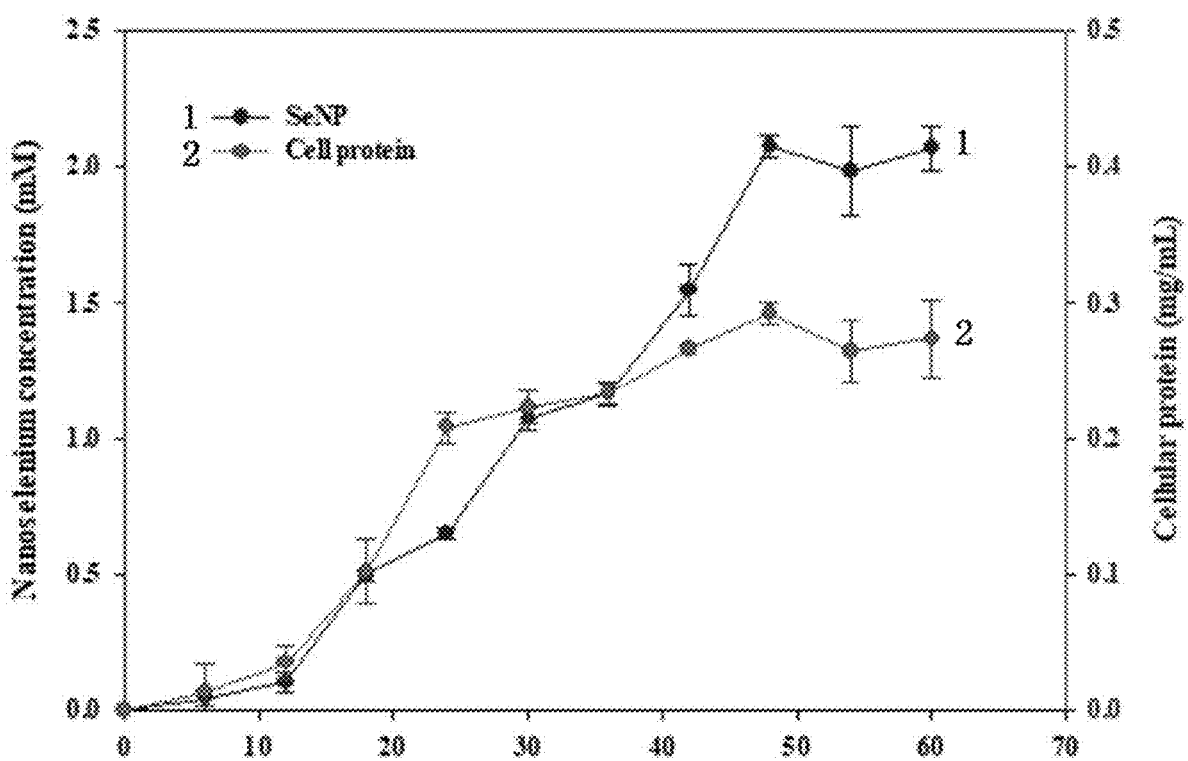
FIG. 4 is a schematic diagram of the biosynthesis of nano-selenium by *E. indicum* YAN2, where the first position of the curve is the yields of nano-selenium at different time points, and the second position of the curve is the cell protein concentrations at the corresponding time points.

The dynamic law of biological nano-selenium synthesis by the strain YAN2 and the dynamic law of cell growth are shown in FIG. 4. From the results in FIG. 4, it can be seen that the strain YAN2 began to synthesize a large amount of nano-selenium after being cultured for 18 h.

Example 5: Analysis on Characteristics of Nano-Selenium Synthesized by *E. indicum*

An activated strain YAN2 was transferred and inoculated into a sterile selenium-containing LB liquid medium according to an amount of inoculation of 2.5±0.2% (v/v), covered with a sealing film, placed in a shaker, and subjected to constant temperature incubation at 30° C. and 150 rpm for 120 h. The bacterial liquid was collected after 120 h of fermentation, and centrifuged at room temperature and 10000 rpm for 6 min; the supernatant was removed, sterile normal saline was added into the precipitate, suspending was fully performed, the product was centrifuged again under the same conditions, the precipitate was collected, and the product was washed twice with normal saline; and finally, the precipitate was suspended in a 2.5% glutaraldehyde solution, and maintained to stand at 4° C. for 12 h for next analysis.

Scanning electron microscope observation: The above-mentioned stationary mixture of nano-selenium and strain was pre-treated (i.e, dehydrated, dried, sprayed with gold), and observed under a scanning electron microscope (Zeiss, EVO-LS10); and the elemental composition of nanoparticles was analyzed by using an energy dispersive spectrometer.

Figure 5:
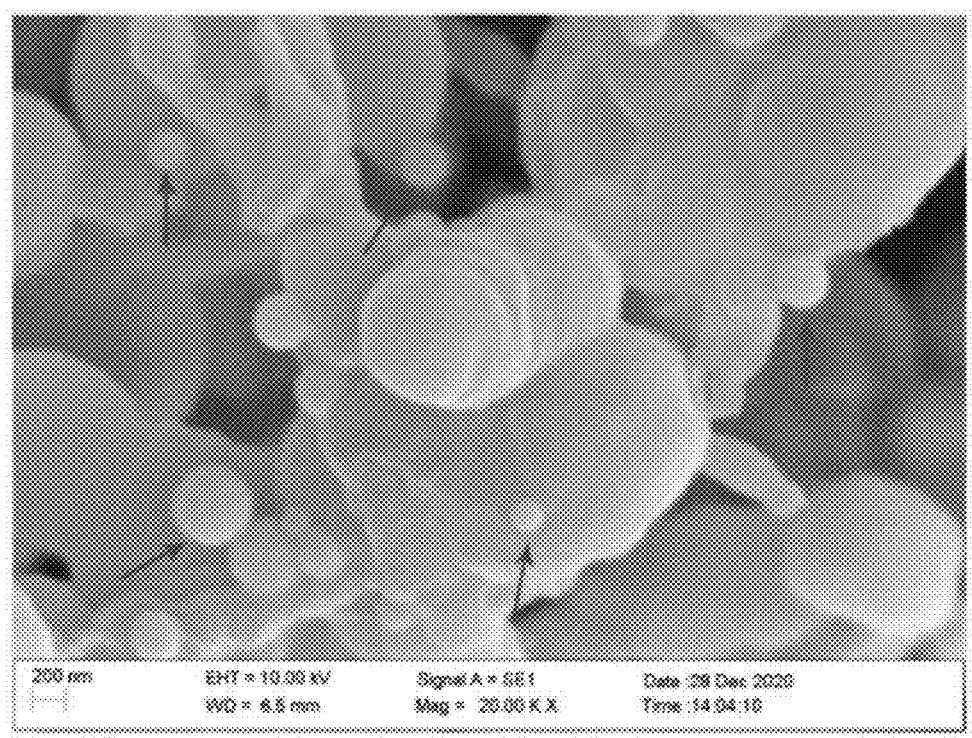
FIG. 5 is a scanning electron microscope (SEM) image of *E. indicum* YAN2 fermented for 120 h to produce nano-selenium.
Figure 6:
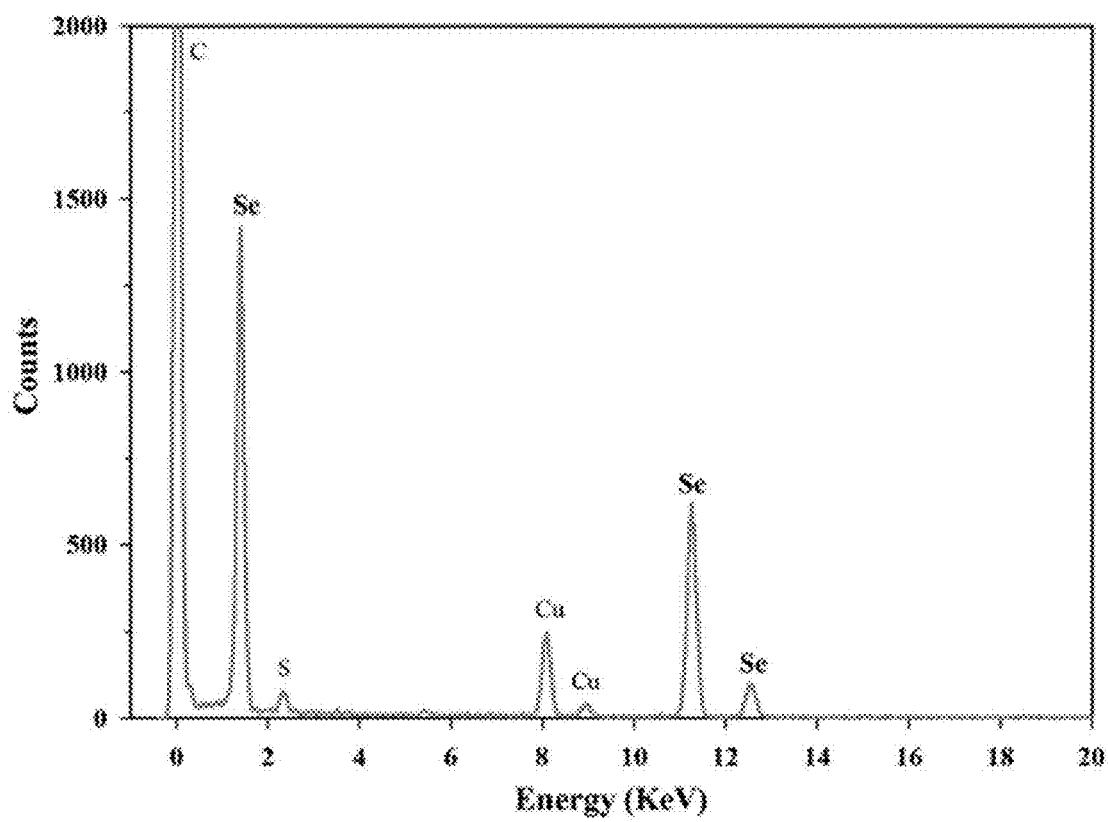
FIG. 6 is an energy dispersive X-ray (EDX) spectrogram of nano-selenium synthesized by *E. indicum* YAN2.

The electron microscope observation results are shown in FIG. 5. Spherical nano-selenium particles can be seen on the YAN2 cells. The particles are distributed in the space around the cells and on the surfaces of the cells, with a particle size distribution range of 160-350 nm. At the same time, the particles are analyzed by EDX energy spectrum, and the results are shown in FIG. 6. The characteristic peaks of selenium (Se) were observed respectively at 1.37, 11.22, and 12.49 keV, which further indicates that sodium selenite is transformed into spherical nanoparticles, i.e., nano-selenium, by the strain YAN2.

This example verifies that the strain YAN2 can efficiently synthesize the spherical nano-selenium.

Example 6: Biosynthesis of Nano-Selenium Liquid Fertilizer Using *E. indicum* YAN2

Preparation of a YAN2 seed solution: *E. indicum* YAN2 was inoculated in an LB liquid medium, and subjected to constant temperature incubation at 28-35° C. and 150-250 rpm until reaching a logarithmic growth phase ($OD_{600}\approx1.0$); centrifugation was performed at 4° C. for collection of bacteria, the bacteria were resuspended in 0.86% sterile normal saline, and the product was stored at 4° C. for later use.

Fermentation in a tank fermentation: A selenium-containing TB fermentation medium, basically composed of a 24 g/L yeast extract, 20 g/L tryptone, 4 ml/L glycerol, 72 mM $K_2HPO_4$, 17 mM $KH_2PO_4$, and 5 mM $Na_2SeO_3$, was employed, with pH being 7.2±0.2; the working volume was 60-70% of the volume of the fermentation tank, and the YAN2 seed solution was inoculated into the fermentation tank according to an amount of inoculation of 2.5±0.2% (v/v); the fermentation temperature was controlled at 30±1° C., the stirring speed was 150±5 rpm, the fermentation volume: the volume of aeration per minute=3:1, and a tank pressure was 1.2±0.2 $F/cm^2$; and after 5-6 d of fermentation, the content (~3.1 mM) of nano-selenium in the fermentation broth inside the tank was measured by using the Biswas method.

Dry nano-selenium powder: The fermentation broth was lowered into the tank and centrifuged at 10000 rpm for 15 min to collect bacterial precipitate, the precipitate was washed with sterile normal saline for 3-4 times (ultrasonic treatment was performed for 10 min after each washing), the obtained precipitate was resuspended with sterile water in an amount being 1/20 of the volume of fermentation broth, and the obtained bacterial suspension was freeze-dried, so that dry nano-selenium powder was obtained.

Nano-selenium liquid fertilizer: The fermentation broth was lowered into the tank and centrifuged at 10000 rpm for 15 min to collect precipitate, the precipitate was washed with sterile normal saline for 3-4 times, and the obtained precipitate was resuspended with sterile water in an amount being 1/20 of the volume of fermentation broth, so that the concentrated nano-selenium liquid fertilizer (with a nano-selenium content being about 60 mM) was finally obtained.

Figure 7:
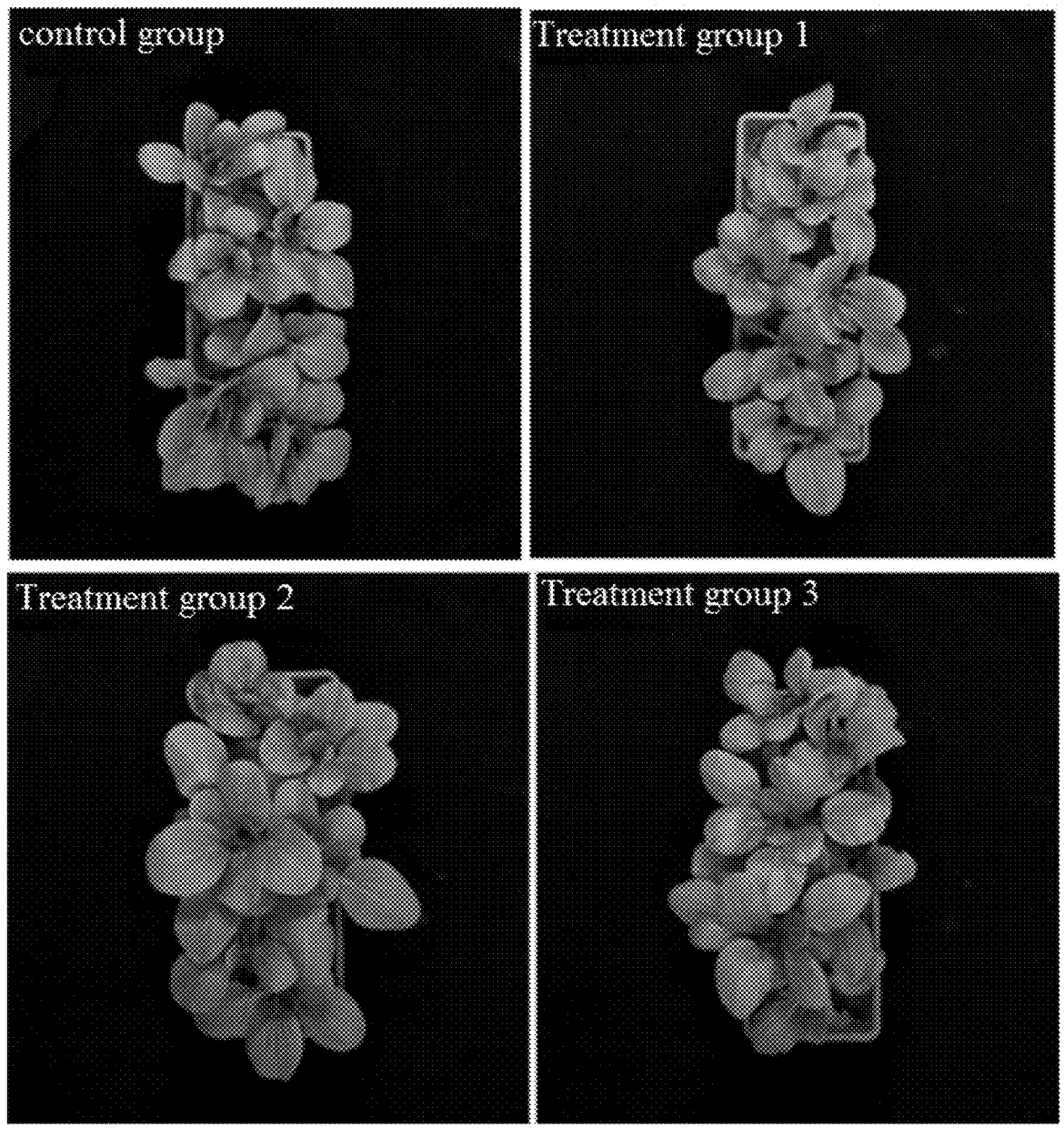
FIG. 7 shows growth photos of small green vegetables applied with different nano-selenium liquid fertilizers, where the concentration of a nano-selenium liquid fertilizer used in treatment group 1 is 1 mg/L; the concentration of a nano-selenium liquid fertilizer used in treatment group 2 is 10 mg/L; the concentration of a nano-selenium liquid fertilizer used in treatment group 3 is 50 mg/L; the spray rate for each of the treatment groups is 60 mL/pot; and the control group is sprayed with an equal volume of deionized water.

Example 7: Growth-Promoting Effect of Biological Nano-Selenium Fertilizer Obtained by Fermenting *E. indicum* YAN2 on Leafy Vegetables Seeds of *Brassica chinensis* L. were purchased from Tomorrow Seed Industry Company, Jiangsu Academy of Agricultural Sciences. The seeds were disinfected by the steps that: first, the seeds were soaked in 70% ethanol for 15 s, then soaked in 2.5% sodium hypochlorite for 15 min, and then rinsed with sterile water. The obtained seeds were transferred to vermiculite and placed in an illumination incubator at 24° C. for accelerating germination. The germinated seeds were sown in test pots, the light cultivation was continued until two true leaves grew out, then thinning was performed, and six uniformly growing seedlings were left in each pot. The above-mentioned prepared nano-selenium fertilizer concentrate was appropriately diluted with deionized water to obtain a nano-selenium liquid fertilizer with a concentration of 1-50 mg/L. The nano-selenium fertilizer was sprayed at the time 15 d earlier than vegetable harvesting. After 45 d of cultivation (see FIG. 7), vegetable samples were collected for analyzing their growth indicators (including plant height, fresh weight, and root activity). The measurement results are shown in Table 2.

TABLE 2

Experimental data on growth-promoting effect of biological nano-selenium fertilizer obtained by fermenting strain YAN2 on green vegetables

| Group | Plant height/cm | Fresh weight/mg | Root activity |
| --- | --- | --- | --- |
| Control group | 28.46 ± 1.09 | 22.67 ± 1.09 | 56.19 ± 6.25 |
| Treatment group 1 | 30.92 ± 2.57 | 23.35 ± 0.95 | 81.42 ± 1.44 |
| Improvement rate | 10.42% | 6.11% | 44.91% |
| Treatment group 2 | 31.58 ± 1.91 | 28.46 ± 4.94 | 61.18 ± 3.80 |
| Improvement rate | 12.80% | 29.35% | 8.89% |
| Treatment group 3 | 30.50 ± 1.00 | 31.59 ± 4.10 | 60.00 ± 5.68 |
| Improvement rate | 8.93% | 43.58% | 6.78% |

Note: The concentration of a nano-selenium liquid fertilizer used in Treatment 1 is 1 mg/L; the concentration of a nano-selenium liquid fertilizer used in Treatment 2 is 10 mg/L; the concentration of a nano-selenium liquid fertilizer used in Treatment 3 is 50 mg/L; the spray rate for each of the treatment groups is 60 mL/pot; and the control group is sprayed with an equal volume of deionized water.

Taking plant height as an example, the improvement rate=(plant height of treatment group-plant height of control group)/plant height of control group×100%.

It can be seen from Table 2 that when 1 mg/L nano-selenium fertilizer (Treatment 1), 10 mg/L nano-selenium fertilizer (Treatment 2), or 50 mg/L nano-selenium fertilizer (Treatment 3) is sprayed, the growth and root activity of green vegetables can be promoted. When the nano-selenium fertilizer is treated at 10 mg/L, the growth-promoting effect is the best; and when the nano-selenium fertilizer is treated at 1 mg/L, the root activity is the strongest.

Example 8: Application of Biological Nano-Selenium Fertilizer Obtained by Fermenting *E. indicum* YAN2 in Improving the Antioxidant Performance of Leafy Vegetables Vegetable seeding and early management are as described in Example 7. After 45 d of cultivation, samples of green vegetables were collected to analyze their antioxidant performance indicators such as peroxidase (POD), superoxide dismutase (SOD), and glutathione peroxidase (GSH-Px). POD, SOD, and GSH-Px kits provided by Nanjing Jiancheng Biological Engineering Research Institute were used for the determination. The determination results are shown in Table 3.

TABLE 3

Experimental data on improving the antioxidant performance of green vegetables by biological nano-selenium fertilizer obtained by fermenting strain YAN2

| Group | POD (U/g fresh weight) | SOD (U/g fresh weight) | GSH-Px (μmol/g fresh weight) |
| --- | --- | --- | --- |
| Control group | 352.00 ± 6.29 | 210.62 ± 21.95 | 455.53 ± 14.14 |
| Treatment group 1 | 465.48 ± 3.70 | 292.66 ± 46.72 | 735.09 ± 14.10 |
| Improvement rate | 32.24% | 38.95% | 61.38% |
| Treatment group 2 | 452.15 ± 1.85 | 311.87 ± 21.87 | 717.54 ± 15.28 |
| Improvement rate | 28.45% | 48.07% | 57.53% |
| Treatment group 3 | 440.30 ± 9.25 | 310.39 ± 41.52 | 665.79 ± 35.12 |
| Improvement rate | 25.08% | 47.37% | 46.17% |

TABLE 4

Experimental data on improving the quality of green vegetables by biological nano-selenium fertilizer obtained by fermenting strain YAN2

| Group | Selenium content (mg/kg fresh weight) | Total phenols (mg/g fresh weight) | Vc content (mg/100 g fresh weight) |
| --- | --- | --- | --- |
| Control group | 0.008 ± 0.001 | 23.33 ± 0.47 | 5.94 ± 0.44 |
| Treatment group 1 | 0.034 ± 0.006 | 30.00 ± 0.82 | 8.67 ± 0.89 |
| Improvement rate | 325% | 28.59% | 45.91% |
| Treatment group 2 | 0.506 ± 0.015 | 26.33 ± 1.25 | 6.77 ± 0.58 |
| Improvement rate | 6231% | 12.87% | 13.93% |

It can be seen from Table 4 that when 1 mg/L nano-selenium fertilizer (Treatment 1), or 10 mg/L nano-selenium fertilizer (Treatment 2) is sprayed, the selenium content, total phenols, and Vc content of green vegetables can be improved. When the treatment concentration of the biological nano-selenium fertilizer is 10 mg/L, the increase in the total selenium content of green vegetables is the most. The increase in the total phenols and Vc content of green vegetables treated with 1 mg/L biological nano-selenium fertilizer is the most.

```
SEQUENCE LISTING

Sequence total quantity: 2
SEQ ID NO: 1           moltype = DNA  length = 20
FEATURE                Location/Qualifiers
source                 1..20
                       mol_type = other DNA
                       organism = synthetic construct
SEQUENCE: 1
agagtttgat cmtggctcag                                                 20

SEQ ID NO: 2           moltype = DNA  length = 19
FEATURE                Location/Qualifiers
source                 1..19
                       mol_type = other DNA
                       organism = synthetic construct
SEQUENCE: 2
ggttaccttg ttacgactt                                                  19
```

It can be seen from Table 3 that when 1 mg/L nano-selenium fertilizer (Treatment 1), 10 mg/L nano-selenium fertilizer (Treatment 2), or 50 mg/L nano-selenium fertilizer (Treatment 3) is sprayed, the antioxidant performance of green vegetables can be improved. Especially, the GSH-Px of the green vegetables is improved the most, followed by SOD. When the nano-selenium fertilizer is treated at 1 mg/L, the improvement effect on POD and GSH-Px is stronger than that of the other two treatments.

Example 9: Application of Biological Nano-Selenium Fertilizer Obtained by Fermenting E. indicum YAN2 in Improving the Quality of Leafy Vegetables Vegetable seeding and early management are as described in Example 7. After 45 d of cultivation, samples of green vegetables were collected to analyze their antioxidant performance indicators such as peroxidase (POD), superoxide dismutase (SOD), and glutathione peroxidase (GSH-Px). The determination results are shown in Table 4.

What is claimed is:

1. A method for synthesizing nano-selenium, comprising:

1) inoculating *Exiguobacterium indicum* with preservation number GDMCC NO. 61594 into a lysogeny broth (LB) liquid medium, and performing activated culture until $OD_{600}$ is approximately equal to 1.0 to obtain activated bacteria liquid;

2) inoculating the activated bacteria liquid obtained in step 1) into a fermentation tank containing a fermentation medium at an amount of inoculation by a volume ratio of 2.5±0.2%, and carrying out fermentation until the bacterial cells content is 0.4-0.6 mg/mL to obtain fermented bacteria liquid, wherein the fermentation medium is prepared by: adding up to 1 L deionized water to 5 g of yeast extract, 10 g of tryptone, and 10 g of NaCl; sterilizing, and then adding 1 M selenite solution to make a final concentration of 5 mM selenite in the medium; and 3) centrifuging the fermented bacteria liquid obtained in step 2), and collecting a precipitate that is the nano-selenium.

2. The method according to claim 1, wherein the fermentation in step 2) refers to a fermentation temperature of 30±1° C., a stirring speed of 150±5 rpm, and a tank pressure being 1.0±0.4 F/cm$^2$.

3. A method for preparing a nano-selenium liquid fertilizer, comprising:
1) inoculating *Exiguobacterium indicum* with preservation number GDMCC NO. 61594 into an LB liquid medium, and performing activated culture until $OD_{600}$ is approximately equal to 1.0 to obtain activated bacteria liquid;
2) inoculating the activated bacteria liquid into a fermentation tank containing a selenium-containing terrific broth (TB) fermentation medium at an amount of inoculation of 2.5±0.2%, and carrying out fermentation to obtain a fermented liquid fertilizer,
wherein the selenium-containing TB fermentation medium is prepared by adding up to 1 L deionized water to 24 g/L of a yeast extract, 20 g/L of tryptone, 4 ml/L of glycerol, 72 mM $K_2HPO_4$, 17 mM $KH_2PO_4$, and 5 mM $Na_2SeO_3$; and
3) centrifuging the fermented liquid fertilizer, and collecting precipitate, washing with sterile normal saline for 3-4 times, and then resuspending the precipitate with sterile water in 1/20 of a volume of the fermented liquid fertilizer, to obtain the nano-selenium liquid fertilizer.

4. The method according to claim 3, wherein the fermentation in step 2) refers to a fermentation temperature of 30±1° C., a stirring speed of 150±5 rpm, and a tank pressure being 1.2±0.2 F/cm$^2$.

* * * * *